United States Patent [19]

Gershman et al.

[11] Patent Number: 4,596,035
[45] Date of Patent: Jun. 17, 1986

[54] METHODS FOR ENUMERATING 3-PART WHITE CELL DIFFERENTIAL CLUSTERS

[75] Inventors: Russell J. Gershman, Middleboro; Irving L. Weiner, Sharon; Arthur C. Daniels, Canton, all of Mass.

[73] Assignee: Ortho Diagnostic Systems Inc., Raritan, N.J.

[21] Appl. No.: 508,448

[22] Filed: Jun. 27, 1983

[51] Int. Cl.⁴ .................... G01N 33/48; G01N 21/64; G06K 9/00
[52] U.S. Cl. .......................................... 382/6; 356/39; 356/340; 356/343
[58] Field of Search .............. 382/6; 356/39, 337–340, 356/343; 377/10, 12; 364/416; 422/68

[56] References Cited

U.S. PATENT DOCUMENTS

| | | | |
|---|---|---|---|
| 3,960,449 | 6/1976 | Carleton et al. | 356/340 |
| 4,070,113 | 1/1978 | Frazer et al. | 356/39 |
| 4,072,421 | 2/1978 | Coyne et al. | 356/39 |
| 4,173,415 | 11/1979 | Wyatt | 356/343 |
| 4,284,412 | 8/1981 | Hansen et al. | 356/39 |

Primary Examiner—Leo H. Boudreau
Attorney, Agent, or Firm—Audley A. Ciamporcero, Jr.; Mark A. Hofer

[57] ABSTRACT

Methods useful for differentiating and enumerating subpopulations of particles in a sample and more particularly relates to the enumeration of leukocyte subclasses. Enumeration is accomplished by utilizing two light scatter parameters and converting these parameters to a single parameter by employing a mathematical, nonlinear transformation.

3 Claims, 5 Drawing Figures

METHODS FOR ENUMERATING 3-PART WHITE CELL DIFFERENTIAL CLUSTERS

FIELD OF THE INVENTION

This invention relates to methods useful for differentiating and enumerating subpopulations of particles in a sample and more particularly relates to the enumeration of leukocyte subclasses.

BACKGROUND OF THE INVENTION

Traditionally, clinical instruments employing flow cytometry methods, i.e., those wherein cells within a sample are hydrodynamically focused to pass in single file fashion through a detection zone illuminated by a focused light source whereby the cells may be distinguished on the basis of their light scattering characteristics, have been used advantageously to derive red cell counts, white cell counts, and platelet counts from, typically, diluted whole blood samples. In an effort to optimize reliability and minimal complexity, such clinical instruments typically have not been provided with the means to enumerate leukocytes subpopulations and in particular enumerate lymphocytes, monocytes, and granulocytes. Heretofore, such enumeration capabilities have generally been limited to research grade instruments because only these instruments, inherently complex due to consumer-investigator versatility requirements, were capable of supporting the additional software and hardware components.

It is an object of the present invention to provide methods whereby the clinical instrument may be easily adapted to perform leukocyte subpopulation enumerations.

It is another object that these methods not rely upon relatively expensive and slow hardware and software means for counting clusters of cells.

It is a further object to employ only a single analog channel for analysis.

It is still another object to provide such capability in a form readily understandable by the ordinary clinical instrument operator.

BRIEF DESCRIPTION OF THE DRAWINGS

Further understanding of the principles and objects of the instant invention may be had by reference to the drawings wherein.

SUMMARY OF THE INVENTION

Figure 1:
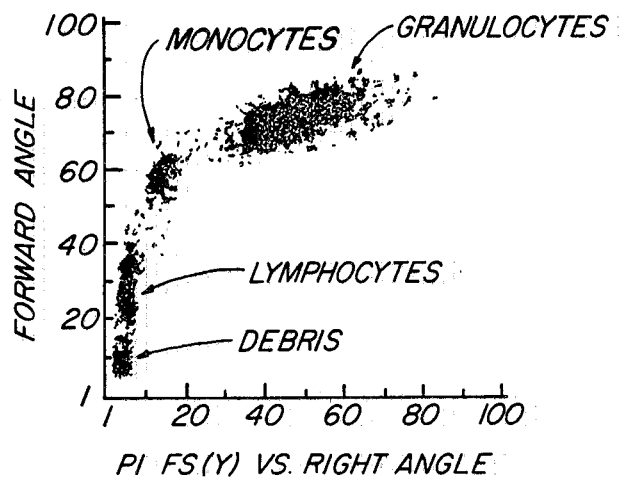
FIG. 1 shows the conventional histogram representation of leukocyte subpopulations based on forward angle and right angle light scatter measurements.

In accordance with the principles and objects of the present invention, there are provided methods for enumerating leukocyte subpopulations without the loss of debris related information. Enumeration is accomplished by utilizing two light scatter parameters and converting these parameters to a single parameter. It has been surprisingly discovered that this may be achieved by employing a mathematical, nonlinear transformation preferably of the form $C(x,y)=(1-mX)bY^{\frac{1}{2}}+aX^2+hX+k$ where X equals the log of the right angle scatter measurement, and Y equals the forward angle scatter measurement. Constants m, b, a, h, and k are chosen pursuant to well-known methods to provide a best fit. Cellular subpopulations distinguished by multiple light scatter parameters may then be enumerated in a single analog channel by counting all the cells located along each line of constant C.

DETAILED DESCRIPTION AND BEST MODE

A typical clinical instrument is the ELT-8 hematology analyzer available from Ortho Diagnostic Systems Inc., Raritan, New Jersey. This instrument is capable of providing RBC (red blood cells or erythrocytes), WBC (white blood cells or leukocytes) and platelet counts, plus the five other traditional parameters HGB, HCT, MCV, MCH, and MCHC. It accomplishes this task by hydrodynamically focusing the blood cells into a sample stream approximately one cell wide for passage through a zone illuminated by a focused light source such as a laser. As each cell passes through the illumination zone, the light is scattered in a manner characteristic for each type of cell. Specifically, the scattered light is detected at substantially forward angle and wide angle locations and leukocytes identified accordingly. The relative wide angle scatter characteristics of different types of leukocytes are relatively insensitive to angles of measurement over at least the range 32° to 148°. Theoretical and experimental considerations [Hansen, et al. "Light Scatter as an Adjunct to Cellular Immunofluorescence in Flow Cytometic Systems", Journal of Clinical Immunology, 2:32s-41s (1982)] indicate that scattering angles below 2° give primarily size information, while angles above 4° are dependent on granularity properties of the cell. The scattered light thusly detected is processed through a single analog channel. As a result, the class of leukocytes (white blood cells) may be differentiated into monocytes, granulocytes and lymphocytes.

In order to meet the demand by clinical laboratories for enumerated leukocyte subpopulations and yet still maintain the clinical instrument in as simple and commercially acceptable form as possible, the inventors hereof have surprisingly discovered a new method of employing a single analog channel to accomplish same. Previously, such cell counts could be accomplished by counting the cells within defined clusters (resulting from the histogram of wide angle scatter versus forward angle scatter shown in FIG. 1). To do this, however, substantial hardware and software would be required in order to accomodate the two parameters, thereby disadvantageously requiring expensive, additional components, operator knowledge and interaction.

Alternately, the histogram as represented in FIG. 1, could be transformed linearly by, rotating the axes thereby moving the clusters but retaining their identical relationship and then, "throwing away" one of the axis in order to reduce the representation to one axis and thereby provide information concerning the numbers of the subpopulations. The linear transformation technique suffers from the disadvantages that there is no single linear transformation which optimizes separation between clusters on the retained histogram axis. In addition, it becomes virtually impossible to retain the debris related information. It is often helpful to examine the debris in order to determine that the instrument is functioning properly and to differentiate the debris from the leukocytes. Although it is unclear at present whether the debris represents clinically important manifestations, a distinct advantage would be gained if such information could be retained for future use as warranted.

Figure 2:
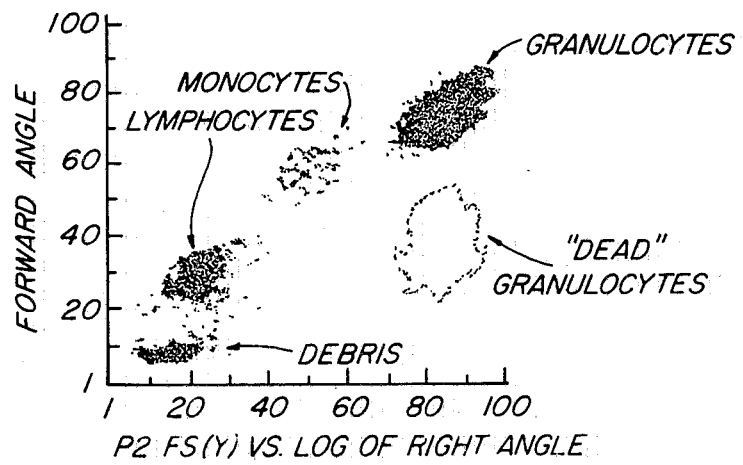
FIG. 2 represents the same histogram based on forward angle and the log of right angle light scatter measurements.

The inventors hereof have surprisingly found that the objects of the present invention may be accomplished by detecting right angle and forward angle light scatter measurements, and reducing these two parameters to a single parameter by employing a nonlinear transformation. Such a technique advantageously provides for the 3-part differential and avoids the disadvantages of the previously discussed methods. By plotting the forward angle scatter measurements against the log of the right angle scatter measurements, the clusters may be rearranged as shown in FIG. 2. The dotted circumscribed area indicates the expected location of "dead" granulocytes which are occasionally found.

By connecting the clusters derived and presented in FIG. 1, it can be shown that the resulting trajectory exhibits a substantially logarithmic relationship. In fact, plotting forward angle scatter against the log of the right angle scatter, shown in FIG. 2, results in greater resolution between clusters and additionally, yields a simpler cluster alignment which may thereafter be more easily manipulated or transformed. The ideal nonlinear transformation function had to maintain this separation and distinction between clusters in a histogram of the single parameter, include the "dead" granulocytes in the granulocyte cluster, and still be analog in nature.

Figure 3:
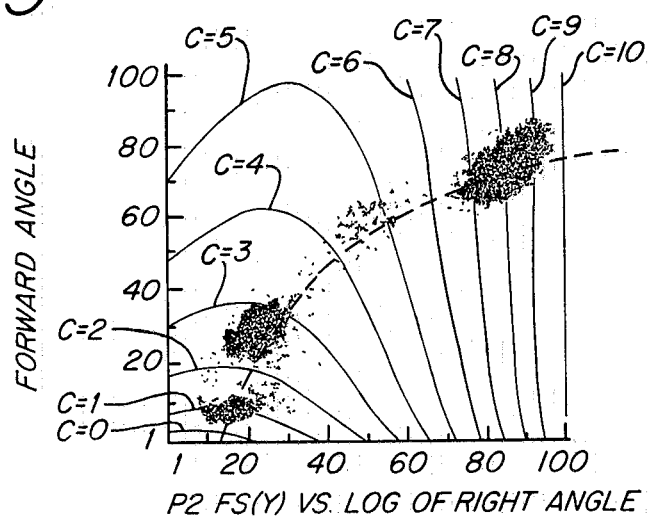
FIG. 3 shows the selection of constant C transformation lines.

The preferred form of the transformation found by the inventors hereof to optimize all of these conditions and objectives is given by:

$$C(x,y) = (1 - mX)by^{\frac{1}{2}} + aX^2 + hX + k$$

where X equals the log of the right angle scatter, Y equals the forward angle scatter measurement and m, b, a, h, and k are constants which are adjusted to provide a best fit. Every cell represented by an x,y pair of values in the histogram of forward scatter versus log of right angle scatter will appear in some channel of the one-dimensional histogram of the transformed parameter $C(x,y)$. A particular channel of the histogram of C, i.e., $C = C_o$, contains as a count, all cells having x,y values which, when transformed by $C(x,y)$, give the same numerical value $C_o$. The transformation may be represented graphically by a family of lines, each line being the locus of x,y values which, when transformed by $C(x,y)$ give identical values of C. FIG. 3 shows typical lines for $C = 0, 1, 2, \ldots, 10$. It is important to note that each C line is substantially perpendicular to the trajectory of the cluster connecting line. Thus, the cells along each C constant line may be counted to provide the desired subpopulation counts. These counts may be readily projected in histogram format as shown in FIG. 4.

Figure 4:
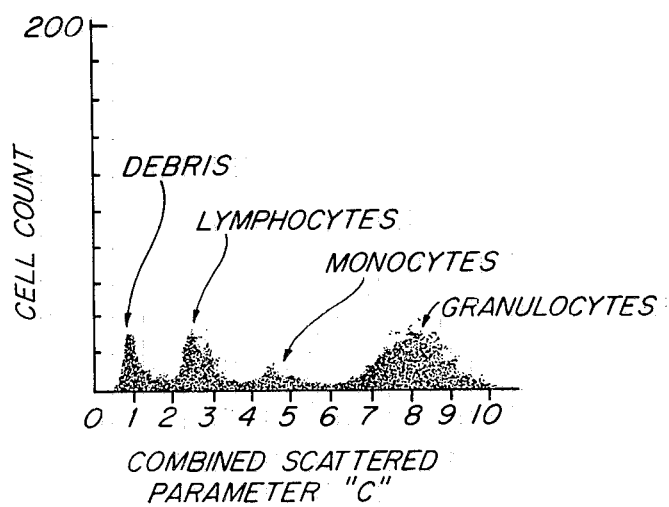
FIG. 4 depicts in histogram fashion the cell counts along the combined scatter parameter C shown in FIG. 3.
Figure 5:
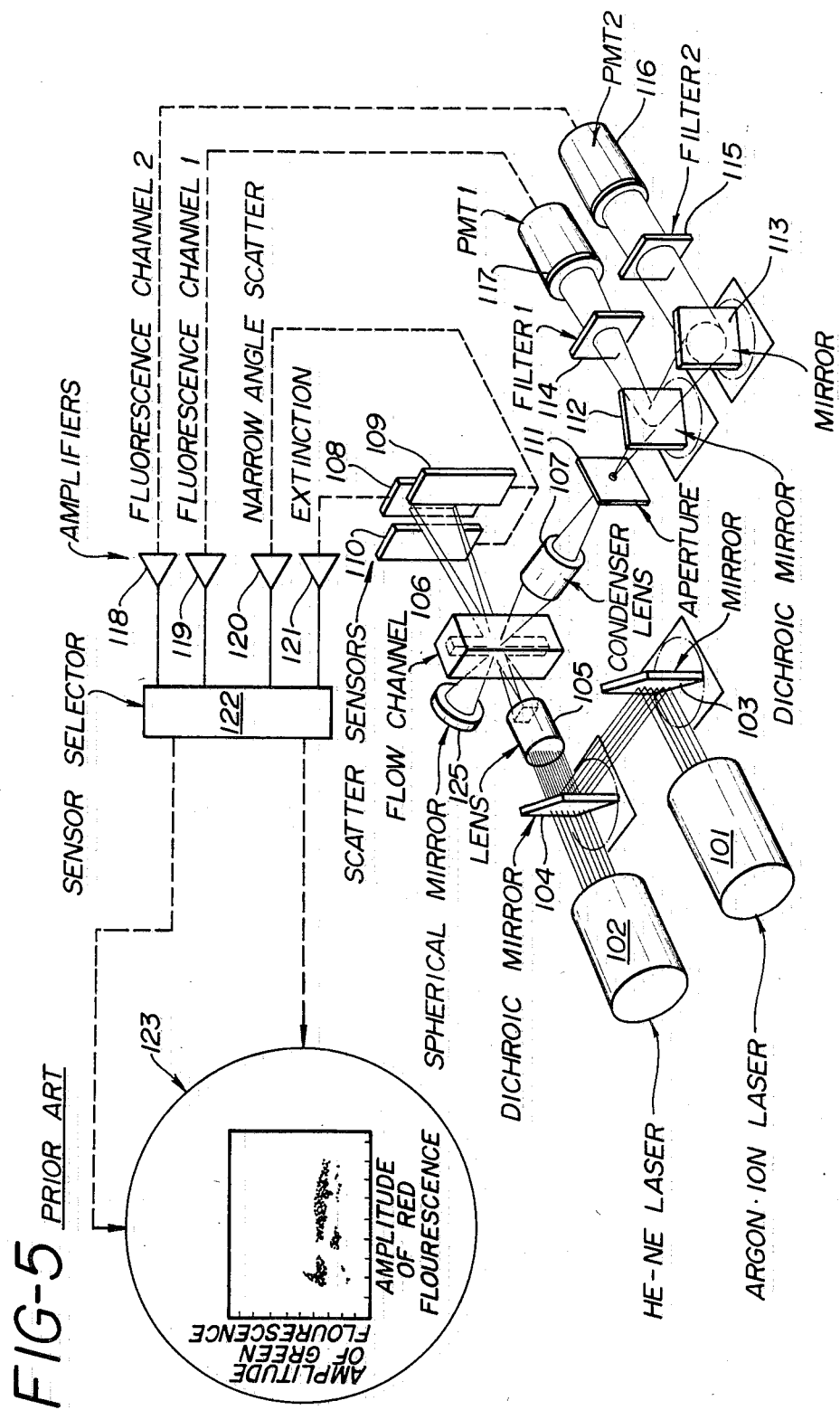
FIG. 5 depicts a prior art system for the automated indentification and enumeration of specified blood cell subclasses.

The numbers on the X axis in FIG. 4 correspond to the values of C drawn on FIG. 3. Thus, for instance, when C equals 8, the line is drawn substantially through the center of the granulocyte cluster and cells falling on said line are counted. The resulting count can then be advantageously projected in the format shown in FIG. 4. Note that the lines of constant C are substantially orthogonal to the trajectory linking the major clusters in order to insure separation of the clusters in the transformed parameter. Additionally, it may be noted that the "dead" granulocytes are included within the granulocyte cluster.

It should be noted that the transformation $C(x,y)$ represents a continuous function combining the forward and right-angle scatter parameters. For small values of C (i.e., $C=0$ to 2) the transform represents mainly the forward scatter component in the vicinity of the debris and lymphocyte clusters. For larger values of C (i.e., $C=7$ to 10), the transform represents mainly right angle scatter. For intermediate values of C (i.e., $C=2$ to 7), the transform represents a continuous and smoothly changing function from forward to right-angle scatter.

It should be further noted that the transformation $C(x,y)$, although implemented in the analog domain in this specific case, is not so limited and may be implemented in the digital domain as well. As may be readily appreciated by those skilled in the art, this may be accomplished by a computer algoritham providing a computer of sufficient speed and capabilities is utilized.

It may now be readily appreciated by those skilled in the art that other nonlinear transformations may be discovered which accomplish similar results, and thus, the principles, spirit and scope of the instant invention are not to be limited to the exact form of the above recited transformation, but include the entire range of equivalents permissable.

What is claimed is:

1. A method for transforming forward light scatter and right angle light scatter parameter measurements into a combined one dimensional parameter for quantifying cellular subclasses of a sample comprising:
   (a) passing the cells, to be differentiated into subpopulations and counted, through a zone illuminated by a focused light source, substantially one at a time;
   (b) detecting light scattered by the passage of said cells through said zone in a substantially forward angle direction;
   (c) further detecting light scattered by the passage of said cells through said zone at a substantially right angle direction whereby each cell may be represented by a forward angle light scatter and a right angle light scatter measurement;
   (d) formulating a trajectory for connecting the cells represented by said forward angle and right angle light scatter measurements;
   (e) determining a series of lines orthogonal to said trajectory describable by a nonlinear function; and
   (f) counting the cells along each of said orthogonal lines whereby cellular subpopulations may be enumerated.

2. A medhod for transforming forward light scatter and right angle light scatter parameter measurements into a combined one dimensional parameter for quantifying cellular subclasses of a sample comprising:
   (a) passing the cells, to be differentiated into subpopulations and counted, through a zone illuminated by a focused light source, substantially one at a time;
   (b) detecting light scattered by the passage of said cells through said zone in a substantially forward angle direction;
   (c) further detecting light scattered by the passage of said cells through said zone at a substantially right angle direction whereby each cell may be represented by a forward angle light scatter and a right angle light scatter measurement;

(d) formulating a trajectory for connecting the cells represented by said forward angle and right angle light scatter measurements;
(e) calculating a series of lines orthogonal to said trajectory pursuant to the nonlinear transformation: $C(x,y) = (1 - mX)bY^{\frac{1}{2}} + aX^2 + hX + k$ where X equals the log of the right angle scatter measurement, Y equals the forward angle scatter measurement, and m, b, a, h, and k are constants chosen to substantially optimize the orthogonality of these lines to said trajectory; and
(f) counting the cells along each line of constant C whereby cellular subpopulations may be enumerated.

3. The method as provided in claim 2 wherein the sample contains leukocytes and the subpopulations to be counted comprise granulocytes, lymphocytes, and monocytes.

* * * * *